(12) United States Patent
Chen

(10) Patent No.: US 9,782,237 B2
(45) Date of Patent: Oct. 10, 2017

(54) METHOD FOR ASSESSMENT OF ORTHODONTIC TREATMENT

(71) Applicant: York S. Y. Chen, Taichung (TW)

(72) Inventor: York S. Y. Chen, Taichung (TW)

(*) Notice: Subject to any disclaimer, the term of this patent is extended or adjusted under 35 U.S.C. 154(b) by 170 days.

(21) Appl. No.: 14/529,215

(22) Filed: Oct. 31, 2014

(65) Prior Publication Data

US 2015/0127266 A1    May 7, 2015

(30) Foreign Application Priority Data

Nov. 6, 2013 (TW) .............................. 102140287 A

(51) Int. Cl.
*A61C 7/00* (2006.01)

(52) U.S. Cl.
CPC .................................... *A61C 7/002* (2013.01)

(58) Field of Classification Search
CPC .. A61C 7/002; A61C 2007/004; G01B 28/20; G01B 21/16
USPC ......................................................... 433/24
See application file for complete search history.

(56) References Cited

U.S. PATENT DOCUMENTS

| | | | |
|---|---|---|---|
| 6,406,292 B1* | 6/2002 | Chishti | A61C 7/00 433/213 |
| 6,783,360 B2* | 8/2004 | Chishti | A61C 7/00 433/6 |
| 7,086,863 B2* | 8/2006 | Van der Zel | A61C 5/10 264/19 |
| 7,220,122 B2* | 5/2007 | Chishti | A61C 7/00 433/24 |
| 7,234,936 B2* | 6/2007 | Lai | A61C 7/08 433/20 |
| 9,622,835 B2* | 4/2017 | See | A61C 7/002 |
| 2005/0019721 A1* | 1/2005 | Chishti | A61C 7/00 433/24 |
| 2005/0191593 A1* | 9/2005 | Knopp | A61C 7/00 433/24 |
| 2006/0099545 A1* | 5/2006 | Lai | A61C 7/00 433/6 |

* cited by examiner

Primary Examiner — Nicholas Lucchesi
(74) Attorney, Agent, or Firm — Trop, Pruner & Hu, P.C.

(57) ABSTRACT

A method for assessment of orthodontic treatment for a patient include: calculating a first feature value according to a facial profile of the patient; calculating a second feature value according to a facial midline of the patient and a mesial surface of one of anterior teeth in an orthodontic quadrant; calculating a space value according to a difference between an arch length of a dental arch portion of the orthodontic quadrant, and a sum of mesiodistal diameters of crowns of teeth encompassed by the dental arch portion; and calculating an assessment value indicating a proposed displacement for a molar in the orthodontic quadrant according to the space value and the first and second feature values.

19 Claims, 7 Drawing Sheets

US 9,782,237 B2

METHOD FOR ASSESSMENT OF ORTHODONTIC TREATMENT

CROSS-REFERENCE TO RELATED APPLICATION

This application claims priority to Taiwanese Application No. 102140287, filed on Nov. 6, 2013.

BACKGROUND OF THE INVENTION

1. Field of the Invention

The invention relates to a method for assessment of orthodontic treatment, and more particularly to a method for assessment of displacement of teeth of a patient.

2. Description of the Related Art

Since different orthodontic patients may encounter different orthodontic problems, it is difficult for a dentist to simply use a fixed pattern to plan orthodontic treatments. In general, the dentist usually needs to determine required displacements of teeth and/or whether a dental extraction is necessary in the orthodontic treatment. If the dental extraction is necessary, the dentist should further determine which tooth should be extracted. Due to the complexity of various orthodontic problems, the dentist usually depends on his/her own clinical experiences to make decisions subjectively.

Conventionally, planning an orthodontic treatment strategy is a process of trial and error. The dentist may finalize the orthodontic treatment strategy based on his/her own experiences and skills, so that the planning process highly depends on subjective judgments and knowledge of the dentist.

SUMMARY OF THE INVENTION

Therefore, an object of the present invention is to provide a method for assessment of orthodontic treatment. The method may be used to propose displacements of teeth based on objective data analysis, so as to assist a dentist in smoothly planning an orthodontic treatment strategy.

According to the present invention, a method is provided for assessment of orthodontic treatment for a patient. The method is to be implemented by a computing device, and comprises the steps of:

calculating, by the computing device, a first feature value according to: a profile analysis line associated with a facial profile of the patient; and a characteristic point of the facial profile of the patient;

calculating, by the computing device, a second feature value according to: a facial midline of the patient; and a mesial surface of one of anterior teeth disposed in a first orthodontic quadrant, which is one of four dental quadrants of the patient;

calculating, by the computing device, a first space value according to a difference between an arch length of a dental arch portion of the first orthodontic quadrant, and a sum of mesiodistal diameters of crowns of teeth that are encompassed by the dental arch portion; and calculating, by the computing device, a first assessment value that indicates a proposed displacement for one of molars that are disposed in the first orthodontic quadrant according to the first feature value, the second feature value and the first space value.

BRIEF DESCRIPTION OF THE DRAWINGS

Other features and advantages of the present invention will become apparent in the following detailed description of an embodiment with reference to the accompanying drawings, of which.

DETAILED DESCRIPTION OF THE EMBODIMENT

Figure 1:
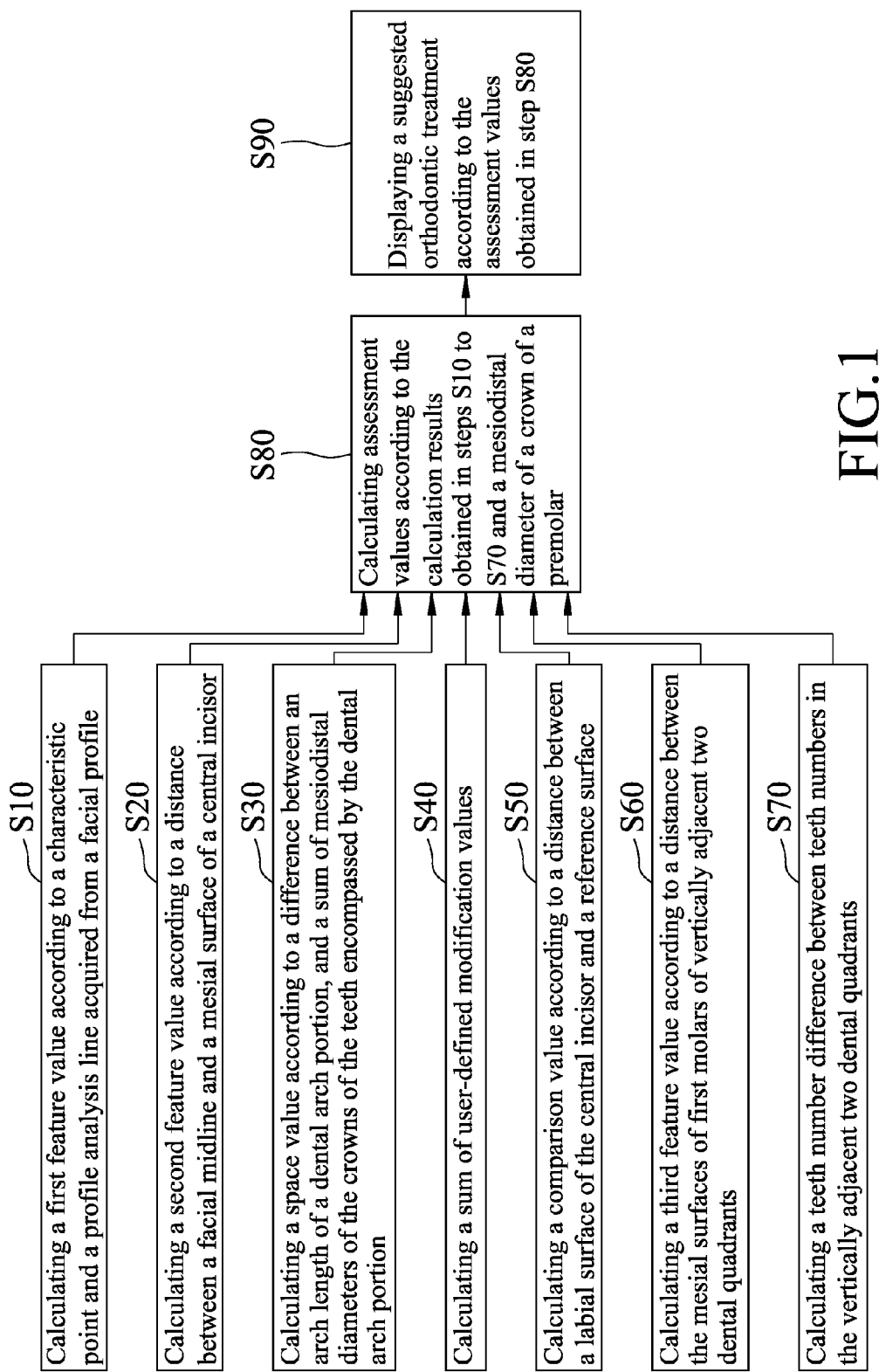
FIG. 1 is a flow chart illustrating an embodiment of a method for assessment of orthodontic treatment for a patient according to the present invention.

Referring to FIG. 1, the embodiment of the method for assessment of orthodontic treatment for a patient according to this disclosure is shown, and is implemented using a computing device (not shown). In application, the computing device may be installed with a software application that includes instructions to enable the computing device to implement the method of the present invention. In this embodiment, the computing device is configured to proceed with assessment of orthodontic treatment according to the following images of the patient: a facial profile image 21 (see FIG. 2), a front facial image 22 (see FIG. 3), a first occlusal image 23 (see FIG. 4) showing occlusal surfaces of maxillary teeth, a second occlusal image 24 (see FIG. 5) showing occlusal surfaces of mandibular teeth, a first dentition image 25 (see FIG. 6) showing a right side view of dentition, and a second dentition image 26 (see FIG. 7) showing a left side view of dentition.

In this embodiment, a three-dimensional (3D) digital scanner, such as 3Shape TRIOS®, is used to generate a 3D image of the teeth of the patient, and the first occlusal image 23, the second occlusal image 24, the first dentition image 25 and the second dentition image 26 are obtained from different viewing angles of the 3D image thus generated. In addition, the facial profile image 21 and the front face image 22 are directly obtained as two-dimensional (2D) images. However, in other embodiments, the first occlusal image 23, the second occlusal image 24, the first dentition image 25 or the second dentition image 26 may be directly obtained as a 2D image.

Figure 2:
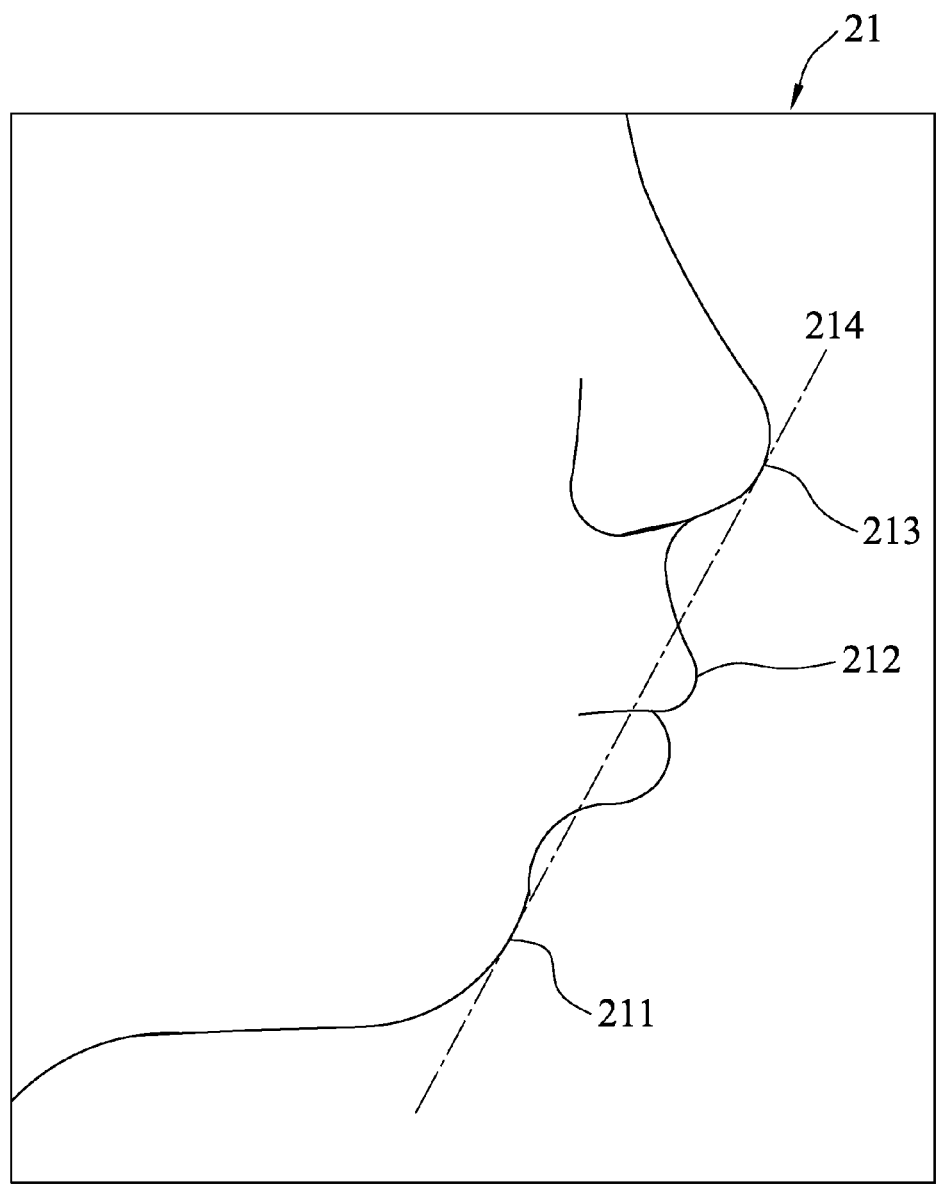
FIG. 2 is a schematic diagram showing a facial profile of the patient.

Further referring to FIG. 2, in step S10, the computing device identifies a chin part as a first characteristic point 211, a front end of lips as a second characteristic point 212, and a nose tip as a third characteristic point 213 according to the facial profile image 21, and obtains a profile analysis line 214 according to the first and third characteristic points 211, 213. The computing device then calculates a first feature value E according to the second first characteristic point 212, the profile analysis line 214 and conventionally acquired aesthetic statistical values. In this embodiment, a positive first feature value E represents that the second characteristic point 212 is proposed to be moved forward, and a negative first feature value E represents that the second characteristic point 212 is proposed to be moved backward. It should be noted that, in the medical field, the aesthetic statistical values may vary according to age, sex, and race of the patient. Table 1 lists the aesthetic statistical values associated with Taiwanese males and females ranging between 11 years and 15 years of age. Note that acquirement of the aesthetic statistical values is conventional knowledge in the art, and details thereof will not be described herein for the sake of brevity. In addition, the profile analysis line 214 may be obtained in a conventional manner, such as Steiner's S line, Burstone's B line, etc., and the present invention should not be limited in this respect.

TABLE 1

| Sex | Age | Aesthetic statistical value |
| --- | --- | --- |
| Male | 11 | 1.5 ± 1.1 |
| Male | 12 | 1.6 ± 1.4 |
| Male | 13 | 1.5 ± 1.2 |
| Male | 14 | 1.8 ± 1.5 |
| Male | 15 | 1.9 ± 1.2 |
| Female | 11 | 1.7 ± 1.5 |
| Female | 12 | 2.0 ± 1.4 |
| Female | 13 | 1.8 ± 1.2 |
| Female | 14 | 1.7 ± 1.3 |
| Female | 15 | 2.0 ± 1.2 |

Figure 3:
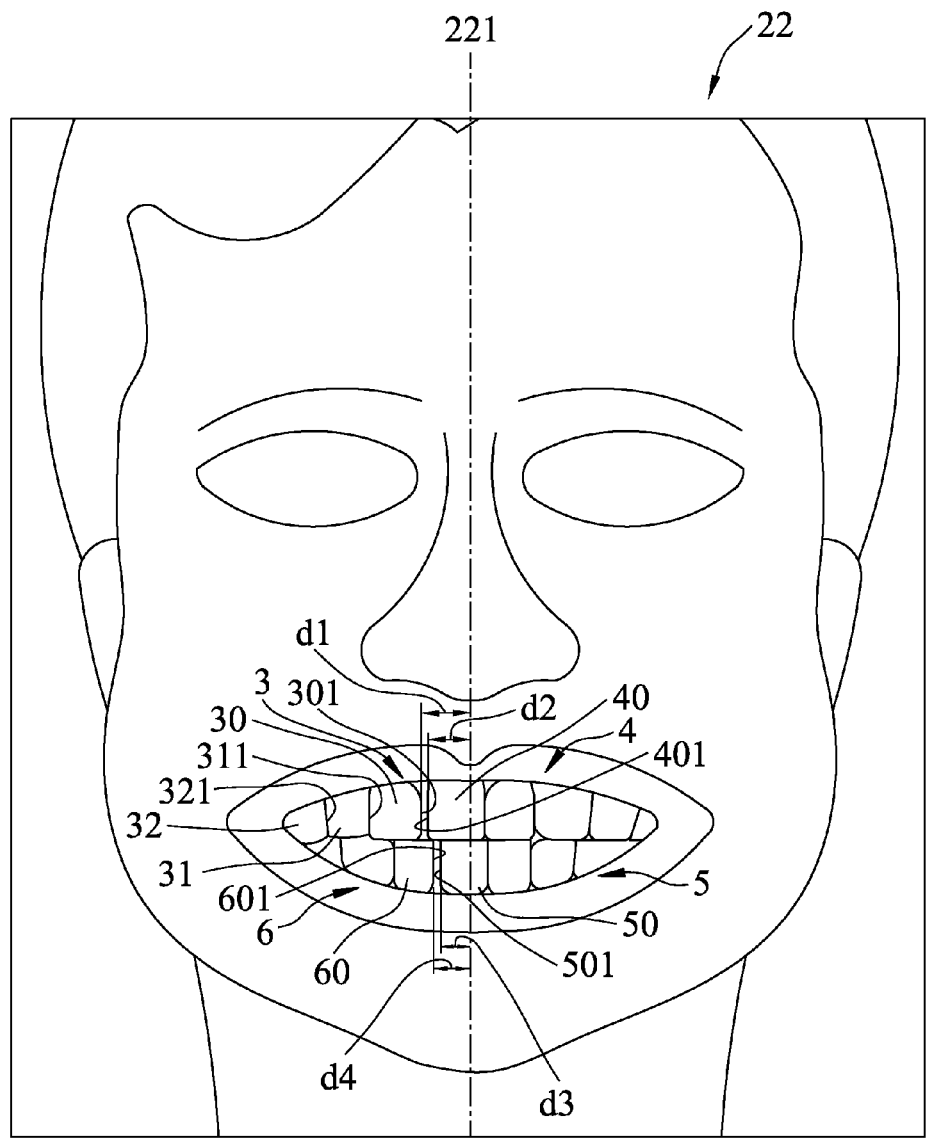
FIG. 3 is a schematic diagram showing a front face of the patient.

Further referring to FIG. 3, in step S20, the computing device identifies a facial midline 221 of the patient according to the front face image 22, identifies, for each of four dental quadrants 3, 4, 5, 6, a mesial surface 301, 401, 501, 601 of a central incisor 30, 40, 50, 60 thereof, and calculates a distance d1, d2, d3, d4 between the mesial surface 301, 401, 501, 601 and the facial midline 221 to serve as a second feature value $L_{H1}$, $L_{H2}$, $L_{L2}$, $L_{L1}$. In this embodiment, a positive second feature value represents that the facial midline 221 passes through the corresponding dental quadrant, and a negative second feature value represents that the facial midline 221 does not pass through the corresponding dental quadrant. Note that the dental quadrants refer to an upper right quadrant (a first quadrant 3), an upper left quadrant (a second quadrant 4), a lower left quadrant (a third quadrant 5) and a lower right quadrant (a fourth quadrant 6) of dentition of the patient, which is well known in the relevant field, and detailed definition thereof is not described herein for the sake of brevity. The first, second, third and fourth quadrants 3, 4, 5, 6 respectively correspond to the subscripts H1, H2, L2, L1 hereinafter. In FIG. 3, since the facial midline 221 passes through the second and third quadrants 4, 5, the second feature values $L_{H1}$ and $L_{L1}$ are negative, and the second feature values $L_{H2}$ and $L_{L2}$ are positive.

It should be noted that, for each of the dental quadrants 3-6, the central incisor 30, 40, 50, 60, the lateral incisor 31, 41, 51, 61 and the canine 32, 42, 52, 62 (i.e., anterior teeth) are respectively the first, second and third candidates for calculating the second feature value. For example, if the patient lacks the central incisor 30, a mesial surface 311 of the lateral incisor 31 may replace the mesial surface 301 of the central incisor 30 in calculating the second feature value $L_{H1}$. If the patient lacks both of the central incisor 30 and the lateral incisor 31, a mesial surface 321 of the canine 32 may replace the mesial surface 301 of the central incisor 30 in calculating the second feature value $L_{H1}$. Such a rule may be applied to all of the dental quadrants 3-6.

Figure 4:
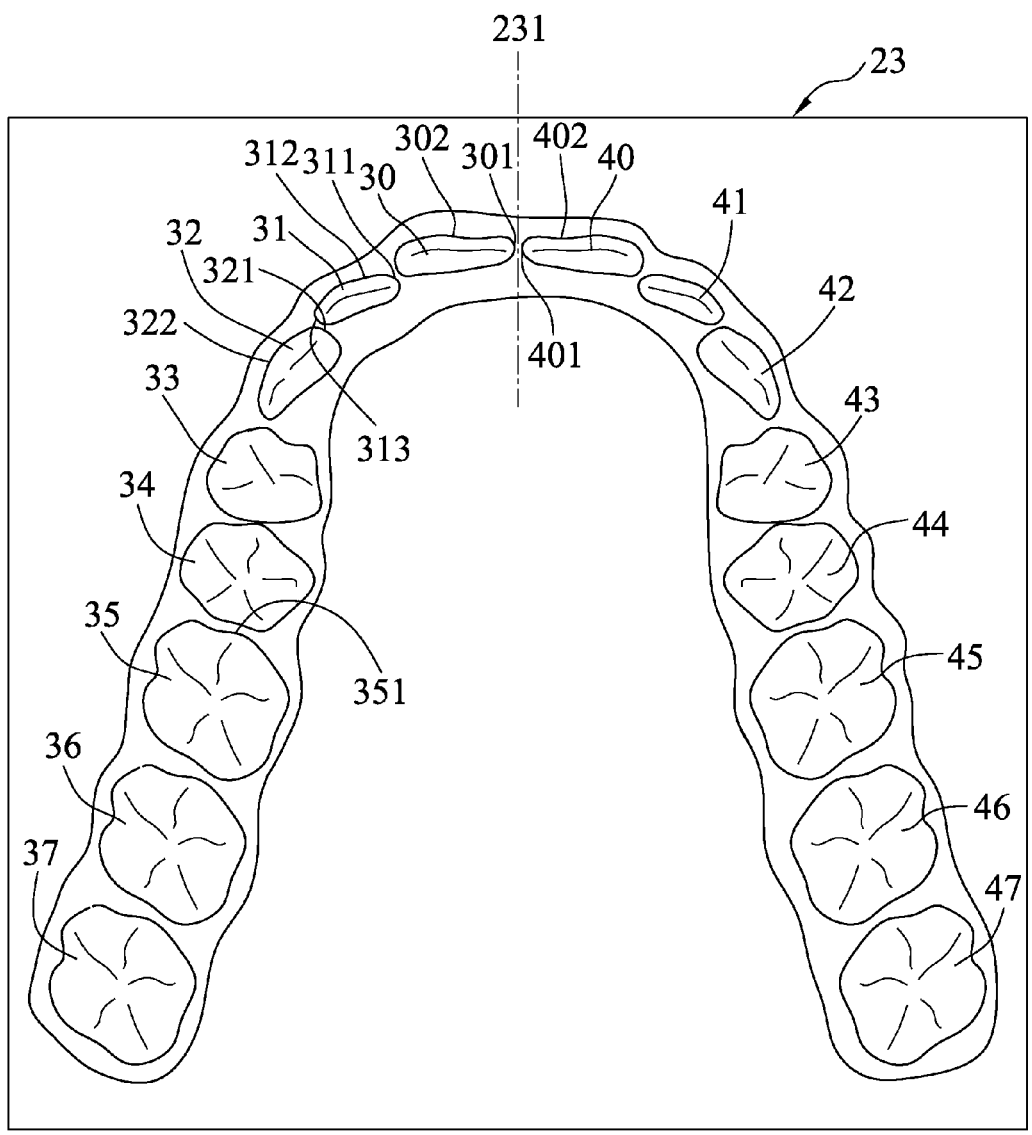
FIG. 4 is a schematic diagram showing occlusal surfaces of maxillary teeth of the patient.
Figure 5:
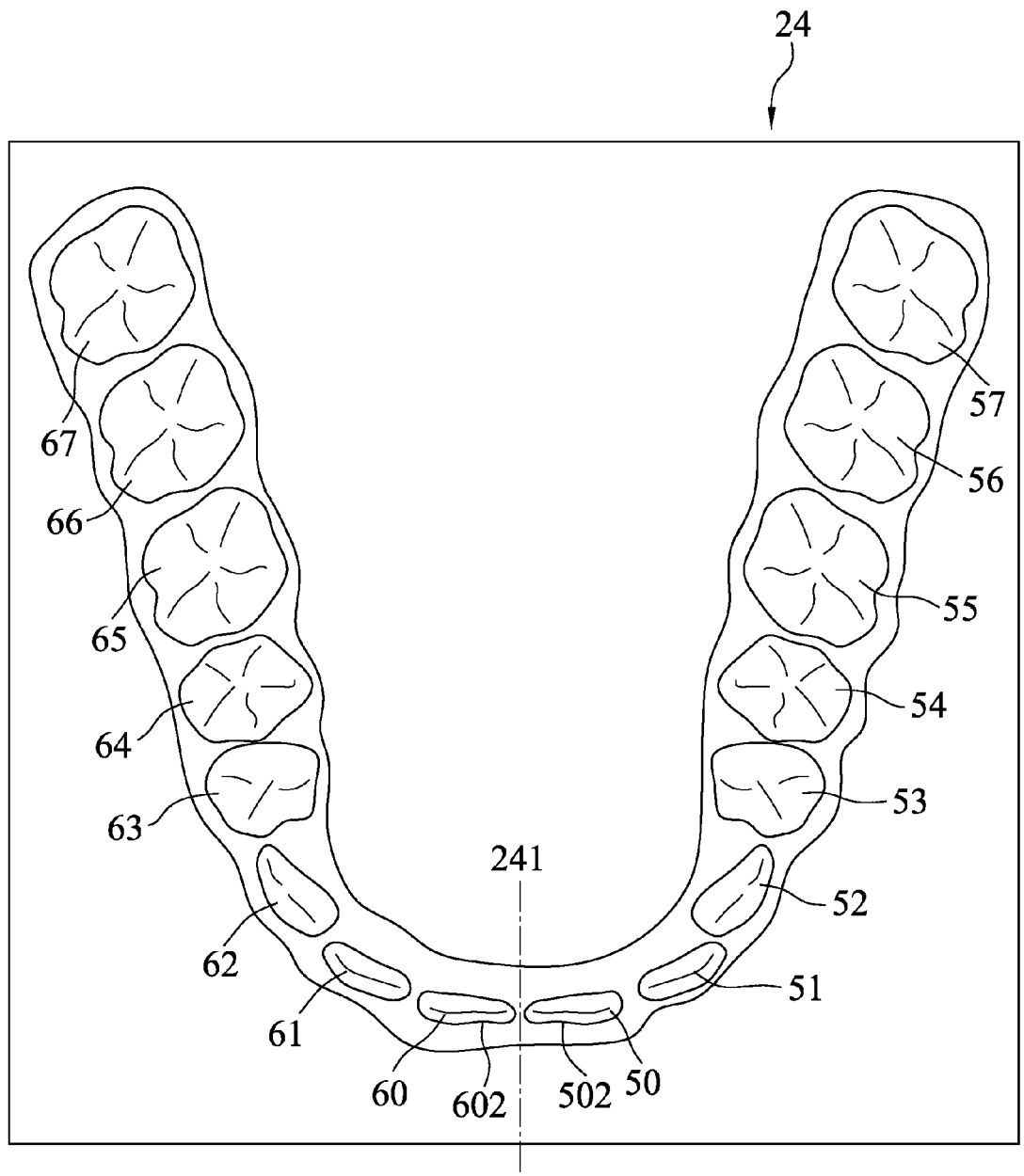
FIG. 5 is a schematic diagram showing occlusal surfaces of mandibular teeth of the patient.

Further referring to FIGS. 4 and 5, in step S30, the computing device identifies, for each of the dental quadrants 3-6, a dental arch portion that is defined to encompass the teeth 31-34, 41-44, 51-54, 61-64, and each of the teeth 31-34, 41-44, 51-54, 61-64 according to the first and second occlusal images 23, 24, acquires an arch length of the dental arch portion, and a mesiodistal diameter of a crown of each of the teeth 31-34, 41-44, 51-54, 61-64, and calculates a difference between the arch length and a sum of the mesiodistal diameters of the crowns of the teeth 31-34, 41-44, 51-54, 61-64 to serve as a space value $S_{H1}$, $S_{H2}$, $S_{L2}$, $S_{L1}$.

In this embodiment, the dental arch portion is defined to be an arch between a dental midline of the patient and a mesial surface of a frontmost one of the molars. That is, the first, second and third molars are respectively the first, second and third candidates for defining the dental arch portion. For example, when the patient has the first molar 35 in the first quadrant 3, the dental arch portion of the first quadrant 3 may be defined to be an arch between a dental midline of the first and second quadrants 3, 4, and a mesial surface 351 of the first molar 35. If the patient lacks the first molar 35, a mesial surface 361 of the second molar 36 may replace the mesial surface 351 of the first molar 35 in defining the dental arch portion of the first quadrant 3. If the patient lacks both of the first and second molars 35, 36, a mesial surface 371 of the second molar 37 may replace the mesial surface 351 of the first molar 35 in defining the dental arch portion of the first quadrant 3. Such a rule may be applied to all of the dental quadrants 3-6.

In this embodiment, for example, the dental midline 231 of the first and second quadrants 3, 4 is defined to be a perpendicular bisector of the mesial surface 301 of the central incisor 30 and the mesial surface 401 of the central incisor 40. However, if the patient lacks the central incisor 30, the mesial surface 311 of lateral incisor 31 may replace the mesial surface 301 of the central incisor 30 in defining the dental midline 231 of the first and second quadrants 3, 4. If the patient lacks both of the central incisor 30 and the lateral incisor 31, the mesial surface 321 of the canine 32 may replace the mesial surface 301 of the central incisor 30 in defining the dental midline 231 of the first and second quadrants 3, 4. Such a rule may be applied to defining the dental midline 241 of the third and fourth quadrants 5, 6. In this embodiment, for example, the arch length of dental arch portion of the first quadrant 3 may be acquired in a conventional manner, such as using a two-part measurement as a sum of: a distance between the mesial surface 301 of the frontmost tooth (i.e., the central incisor 30), and a distal surface 313 of the lateral incisor 31; and a distance between the distal surface 313 of the lateral incisor 31, and the mesial surface 351 of the first molar 35. Such a manner may be applied to acquirement of the arch length of the dental arch portions of all of the dental quadrants 3-6. However, the present invention should not be limited in this respect, and the arch length may be acquired in a manner of a three-part measurement, or measuring a length of a curve that is substantially drawn along the dental arch. Note that since definitions of the mesial surface, the distal surface and the mesiodistal diameter are well known in the relevant field, details thereof are not described herein for the sake of brevity.

In step S40, the computing device generates a user interface for a user (e.g., an orthodontic dentist) to input user-defined modification values that respectively indicate intended changes in mesiodistal diameters of all of the teeth for each of the dental quadrants 3-6, and calculates, for each of the dental quadrants 3-6, a sum $B_{H1}$, $B_{H2}$, $B_{L2}$, $B_{L1}$ of the user-defined modification values. In this embodiment, a positive user-defined modification value represents the mesiodistal diameter of the corresponding tooth is intended to be wider, and a negative user-defined modification value represents the mesiodistal diameter of the corresponding tooth is intended to be narrower.

In step S50, the computing device identifies the central incisors 30, 40 according to the first occlusal image 23, defines a front one of labial surfaces 302, 402 of the central incisors 30, 40 as a reference surface, and calculates a distance between the labial surface 302 and the reference surface to serve as a comparison value $C_{H1}$, and a distance between the labial surface 402 and the reference surface to serve as a comparison value $C_{H2}$.

It should be noted that, when the central incisor 30 or the central incisor 40 is angularly crooked, the crooked incisor should be rotated to a regular position in a virtual manner (e.g., computer simulation) for calculating the comparison values $C_{H1}$, $C_{H2}$. If the patient lacks the central incisor 30, a labial surface 312 of the lateral incisor 31 may replace the labial surface 302 of the central incisor 30 in calculating the comparison value $C_{H1}$. If the patient lacks both of the central incisor 30 and the lateral incisor 31, a labial surface 322 of the canine 32 may replace the labial surface 302 of the central incisor 30 in calculating the comparison value $C_{H1}$. Such a rule may be applied to calculation of the comparison value $C_{H2}$.

Figure 6:
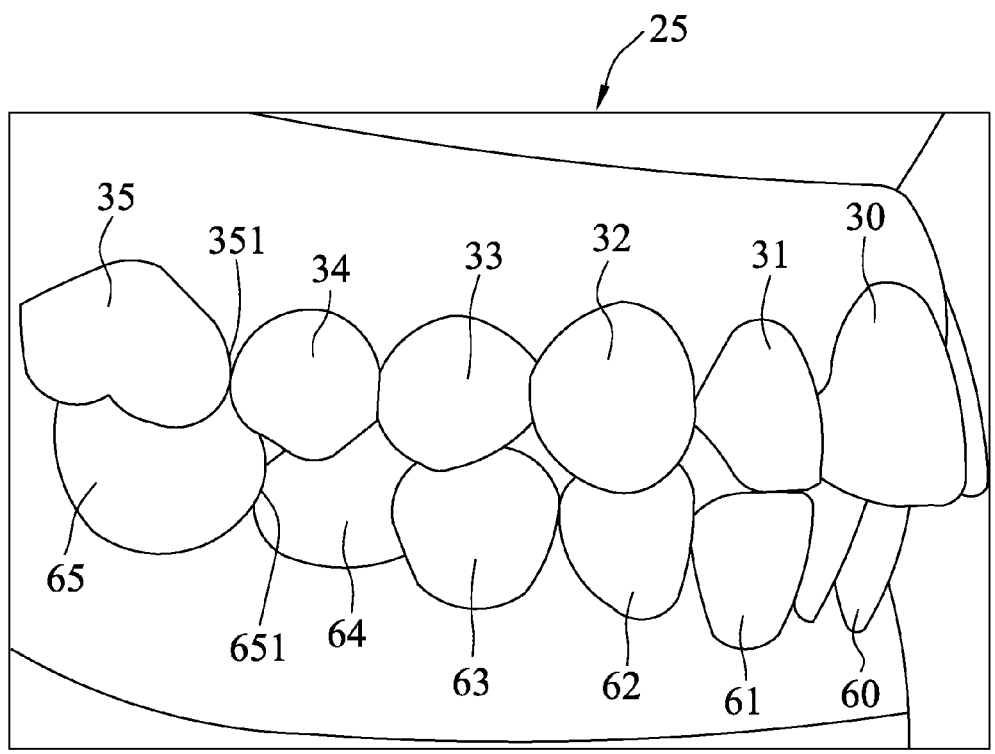
FIG. 6 is a schematic diagram showing aright side of dentition of the patient.
Figure 7:
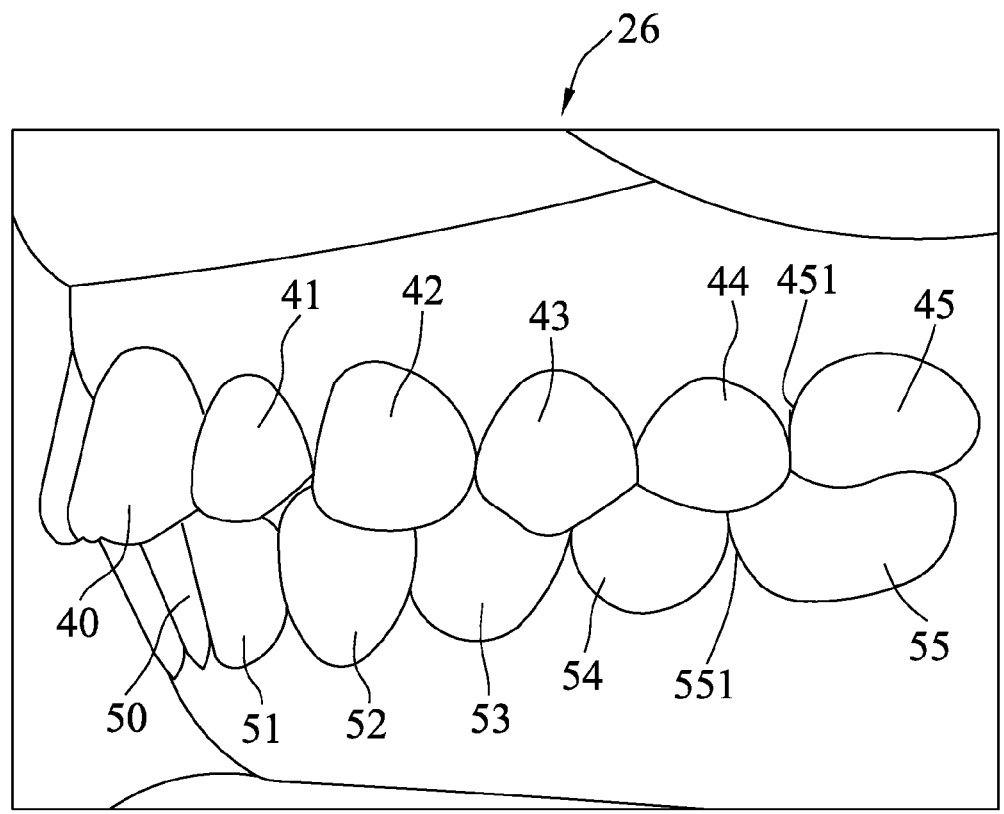
FIG. 7 is a schematic diagram showing a left side of the dentition of the patient.

Further referring to FIGS. 6 and 7, in step S60, the computing device identifies mesial surfaces 351, 651 of the frontmost one of the molars (i.e., the first molar 35, 65) of the first and fourth quadrants 3, 6 according to the first dentition image 25, identifies mesial surfaces 451, 551 of the frontmost one of the molars (i.e., the first molar 45, 55) of the second and third quadrants 4, 5 according to the second dentition image 26, and calculates a distance between the mesial surfaces 351, 651, and a distance between the mesial surfaces 451, 551 to respectively serve as third feature values $D_1$, $D_2$. In this embodiment, a positive third feature value $D_1$ represents that the mesial surface 351 is disposed at a mesial side of the mesial surface 651, a negative third feature value $D_1$ represents that the mesial surface 351 is disposed at a distal side of the mesial surface 651, a positive third feature value $D_2$ represents that the mesial surface 451 is disposed at the mesial side of the mesial surface 551, and a negative third feature value $D_2$ represents that the mesial surface 451 is disposed at the distal side of the mesial surface 551.

In step S70, the computing device identifies each of the teeth of the patient according to the first and second dentition images 25, 26, acquires, for each of the dental quadrants 3-6, a teeth number of teeth excluding the molars 35-37, 45-47, 55-57, 65-67, and calculates a teeth number difference $N_1$ between the teeth numbers in the first and fourth quadrants 3, 6, and a teeth number difference $N_2$ between the teeth numbers in the second and third quadrants 4, 5.

In step S80, the computing device acquires, for each of the dental quadrants 3-6, a mesiodistal diameter $P_{H1}$, $P_{H2}$, $P_{L2}$ and $P_{L1}$ of the crown of a frontmost one of premolars 33-34, 43-44, 53-54, 63-64, and calculates, for each of the dental quadrants 3-6, an assessment value $M_{H1}$, $M_{H2}$, $M_{L2}$ and $M_{L1}$ that indicates a proposed displacement for the frontmost one of the molars 35-37, 45-47, 55-57, 65-67, and calculates, for each of the dental quadrants 3-6, an assessment value $I_{H1}$, $I_{H2}$, $I_{L2}$ and $I_{L1}$ that indicates a proposed displacement for the frontmost one of the anterior teeth 30-32, 40-42, 50-52, 60-62 according to the following equations (1) to (4):

$$M_{Hi} = \frac{E}{A} + P_{Hi} - L_{Hi} - S_{Hi} - B_{Hi} + C_{Hi}, \; i = 1 \text{ or } 2 \quad (1)$$

$$M_{Li} = M_{Hi} + D_i + P_{Hi} \times \left(N_i + \frac{1}{2}\right), \; i = 1 \text{ or } 2 \quad (2)$$

$$I_{Hi} = \frac{E}{A} + C_{Hi}, \; i = 1 \text{ or } 2 \quad (3)$$

$$I_{Li} = -(P_{Li} - M_{Li} - L_{Li} - S_{Li} - B_{Li}), \; i = 1 \text{ or } 2 \quad (4)$$

where A is a predetermined constant. Note that movement of the frontmost tooth in the first and second quadrants 3, 4 may result in movement of the second characteristic point 212. In this embodiment, the constant A is 0.7, which is an estimated ratio of a distance of the movement of the second characteristic point 212 to a distance of the movement of the frontmost tooth in the first and second quadrants 3, 4.

In other words, as an example, for the first quadrant 3, when the patient has the first molar 35, $M_{H1}$ indicates the proposed displacement of the first molar 35. If the patient lacks the first molar 35, $M_{H1}$ may indicate the proposed displacement of the second molar 36. If the patient lacks both of the first and second molars 35, 36, $M_{H1}$ may indicate the proposed displacement of the third molar 37. When the patient has the central incisor 30, $I_{H1}$ indicates the proposed displacement of the central incisor 30. If the patient lacks the central incisor 30, $I_{H1}$ may indicate the proposed displacement of the lateral incisor 31. If the patient lacks both of the central incisor 30 and the lateral incisor 31, $I_{H1}$ may indicate the proposed displacement of the canine 32. When the patient has the first premolar 33, $P_{H1}$ represents the mesiodistal diameter of the crown of the first premolar 33. If the patient lacks the first premolar 33, $P_{H1}$ may represent the mesiodistal diameter of the crown of the second premolar 34. Such rules may be applied to all of the dental quadrants 3-6. In this embodiment, a positive assessment value $M_{H1}$, $M_{H2}$, $M_{L2}$ and $M_{L1}$ represents that the corresponding molar is proposed to be moved toward a mesial direction, a negative assessment value $M_{H1}$, $M_{H2}$, $M_{L2}$ and $M_{L1}$ represents that the corresponding molar is proposed to be moved toward a distal direction, a positive assessment value $I_{H1}$, $I_{H2}$, $I_{L2}$ and $I_{L1}$ represents that the corresponding one of the anterior teeth is proposed to be moved toward the mesial direction, and a negative assessment value $I_{H2}$, $I_{H2}$, $I_{L2}$ and $I_{L1}$ represents that the corresponding one of the anterior teeth is proposed to be moved toward the distal direction.

Finally, in step S90, the computing device displays, for each of the dental quadrants 3-6, a suggested orthodontic treatment according to the assessment values obtained in step S80, more particularly, according to the assessment values $M_{H1}$, $M_{H2}$, $M_{L2}$ and $M_{L1}$. The suggested orthodontic treatments may be determined according to a predetermined table that contains various orthodontic treatments respectively corresponding to different intervals of the assessment values.

In this embodiment, the user interface generated by the computing device is further configured to display the images 21-26 and the suggested orthodontic treatments respectively corresponding to the dental quadrants 3-6. The characteristic points 211-213, the facial midline 221, each (surface) of the teeth, and the dental arch portions may be identified/defined by user operation of the computing device (e.g., by clicking a mouse button according to the images 21-26 displayed by the computing device). However, in other embodiments, the characteristic points 211-213, the facial midline 221, each of the teeth, and the dental arch portions may be identified/defined using conventional image recognition technology, and the present invention should not be limited in this respect.

In summary, the method of the present disclosure is implemented by the computing device to calculate the first feature value E, the second feature values $L_{H1}$, $L_{H2}$, $L_{L2}$, $L_{L1}$, the space values $S_{H1}$, $S_{H2}$, $S_{L2}$, $S_{L1}$, the sums $B_{H1}$, $B_{H2}$, $B_{L2}$, $B_{L1}$ of the user-defined modification values, the comparison values $C_{H1}$, $C_{H2}$, the third feature values $D_1$, $D_2$, and the teeth number differences $N_1$, $N_2$, so as to further calculate the assessment values $M_{H1}$, $M_{H2}$, $M_{L2}$, $M_{L1}$, $I_{H1}$, $I_{H2}$, $I_{L2}$ and $I_{L1}$, and to provide suggested orthodontic treatments for assisting the orthodontic dentist in determining the orthodontic treatment strategy using objective data analysis, thereby promoting smoothness and precision of planning the orthodontic treatment strategy.

While the present invention has been described in connection with what is considered the most practical embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for displacing teeth to improve the appearance of a patient's teeth comprising:
   displacing, using an orthodontic apparatus, the patient's molar based on a first assessment value that indicates a displacement of the molar disposed in a first orthodontic quadrant according to a first feature value, a second feature value and a first space value;
   wherein the first feature value corresponds to a profile analysis line associated with a facial profile of the patient; and a characteristic point of the facial profile of the patient;
   wherein the second feature value corresponds to a facial midline of the patient and a mesial surface of one of anterior teeth disposed in a first orthodontic quadrant, which is one of four dental quadrants of the patient; and
   wherein the first space value corresponds to a difference between an arch length of a dental arch portion of the first orthodontic quadrant, and a sum of mesiodistal diameters of crowns of teeth that are encompassed by the dental arch portion.

2. The method according to claim 1, wherein the dental arch portion is defined to be an arch between a dental midline of the patient and a mesial surface of a frontmost one of the molars in the first orthodontic quadrant, and the first assessment value indicates the proposed displacement for the frontmost one of the molars.

3. The method according to claim 1, wherein the first assessment value further corresponds to a mesiodistal diameter of a crown of one of premolars that are disposed in the first orthodontic quadrant.

4. The method according to claim 1, wherein the profile analysis line is obtained according to a nose tip and a chin part of the facial profile of the patient, and the characteristic point is a front end of lips of the facial profile of the patient.

5. The method according to claim 1, wherein the first assessment value further corresponds to a mesiodistal diameter of a crown of one of premolars that are disposed in the first orthodontic quadrant; and a sum of user-defined modification values that respectively indicate intended changes in mesiodistal diameters of teeth that are disposed in the first orthodontic quadrant.

6. The method according to claim 5, a labial surface of one of anterior teeth in two laterally adjacent ones of the four dental quadrants being defined to be a reference surface, the two laterally adjacent ones of the four dental quadrants including the first orthodontic quadrant, said method further comprising:
   calculating, by a computing device, a comparison value according to a distance between the reference surface and the labial surface of one of anterior teeth that are disposed in the first orthodontic quadrant;
   wherein the computing device calculates the first assessment value further according to the comparison value.

7. The method according to claim 6, wherein the computing device calculates the first assessment value according to:

$$M_{H1} = \frac{E}{A} + P_{H1} - L_{H1} - S_{H1} - B_{H1} + C_{H1}$$

where $M_{H1}$ represents the first assessment value, E represents the first feature value, A is a predetermined constant, $P_{H1}$ represents the mesiodistal diameter of the crown of said one of the premolars that are disposed in the first orthodontic quadrant, $L_{H1}$ represents the second feature value, $S_{H1}$ represents the first space value, $B_{H1}$ represents the sum of the user-defined modification values, and $C_{H1}$ represents the comparison value.

8. The method according to claim 1, further comprising the steps of:
   calculating, by a computing device, a third feature value according to a distance between a mesial surface of a frontmost one of the molars disposed in the first orthodontic quadrant, and a mesial surface of a frontmost one of molars disposed in a second orthodontic quadrant, which is another one of the four dental quadrants of the patient and which is vertically adjacent to the first orthodontic quadrant;
   obtaining, by the computing device, a teeth number difference between a number of teeth in the first orthodontic quadrant excluding the molars, and a number of teeth in the second orthodontic quadrant excluding the molars; and
   calculating, by the computing device, a second assessment value that indicates a proposed displacement for one of the molars that are disposed in the second orthodontic quadrant according to the first assessment value, the third feature value, a mesiodistal diameter of a crown of one of premolars that are disposed in the first orthodontic quadrant, and the teeth number difference.

9. The method according to claim 8, wherein the computing device calculates the second assessment value according to:

$$M_{L1} = M_{H1} + D_1 + P_{H1} \times (N_1 + \tfrac{1}{2})$$

where $M_{L1}$ represents the second assessment value, $M_{H1}$ represents the first assessment value, $D_1$ represents the third feature value, $P_{H1}$ represents the mesiodistal diameter of the crown of said one of the premolars that are disposed in the first orthodontic quadrant, and $N_1$ represents the teeth number difference.

10. The method according to claim 8, further comprising:
   calculating, by the computing device, a fourth feature value according to a distance between the facial midline and a mesial surface of one of anterior teeth that are disposed in the second orthodontic quadrant;
   calculating, by the computing device, a second space value according to a difference between an arch length of a dental arch portion of the second orthodontic quadrant, and a sum of mesiodistal diameters of crowns of teeth that are encompassed by the dental arch portion of the second orthodontic quadrant; and
   calculating, by the computing device, a third assessment value that indicates a proposed displacement for one of the anterior teeth that are disposed in the second orthodontic quadrant according to the fourth feature value, the second space value and the second assessment value.

11. The method according to claim 10, wherein the computing device calculates the third assessment value further according to a mesiodistal diameter of a crown of one of premolars that are disposed in the second orthodontic quadrant.

12. The method according to claim 10, wherein the computing device calculates the third assessment value further according to a sum of user-defined modification values that respectively indicate intended changes in mesiodistal diameters of teeth that are disposed in the second orthodontic quadrant.

13. The method according to claim 12, wherein the computing device calculates the third assessment value further according to a mesiodistal diameter of a crown of one of premolars that are disposed in the second orthodontic quadrant.

14. The method according to claim 13, wherein the computing device calculates the third assessment value according to:

$$I_{L1} = -(P_{L1} - M_{L1} - L_{L1} - S_{L1} - B_{L1})$$

where $I_{L1}$ represents the third assessment value, $P_{L1}$ represents the mesiodistal diameter of the crown of one of the premolars that are disposed in the second orthodontic quadrant, $M_{L1}$ represents the second assessment value, $L_{L1}$ represents the fourth feature value, $S_{L1}$ represents the second space value, and $B_{L1}$ represents the sum of the user-defined modification values.

15. The method according to claim 1, further comprising:
displaying a suggested orthodontic treatment according to the first assessment value.

16. The method according to claim 1, a labial surface of one of anterior teeth in two laterally adjacent ones of the four dental quadrants being defined to be a reference surface, the two laterally adjacent ones of the four dental quadrants including the first orthodontic quadrant, said method further comprising:
calculating, by a computing device, a comparison value according to a distance between the reference surface and the labial surface of one of anterior teeth that are disposed in the first orthodontic quadrant; and
calculating, by the computing device, a second assessment value that indicates a proposed displacement for one of anterior teeth that are disposed in the first orthodontic quadrant according to the first feature value and the comparison value.

17. The method according to claim 16, wherein the computing device calculates the second assessment value according to:

$$I_{H1} = \frac{E}{A} + C_{H1}$$

where $I_{H1}$ represents the second assessment value, E represents the first feature value, A is a predetermined constant, and $C_{H1}$ represents the comparison value.

18. A method for patient treatment comprising:
displacing, using an orthodontic apparatus, an anterior tooth based on an assessment value that indicates a displacement of the anterior tooth disposed in an orthodontic quadrant according to a feature value and comparison value;
wherein the feature value corresponds to a profile analysis line associated with a facial profile of the patient; and a characteristic point of the facial profile of the patient; and
wherein the comparison value corresponds to a distance between a labial surface of one of anterior teeth that are disposed in an orthodontic quadrant, which is one of four dental quadrants of the patient, and a reference surface, wherein a labial surface of one of anterior teeth in two laterally adjacent ones of the four dental quadrants is defined to be the reference surface, and the two laterally adjacent ones of the four dental quadrants include the orthodontic quadrant.

19. The method according to claim 18, further including using a computing device to calculate the assessment value according to:

$$I_{H1} = \frac{E}{A} + C_{H1}$$

where $I_{H1}$ represents the assessment value, E represents the feature value, A is a predetermined constant, and $C_{H1}$ represents the comparison value.

* * * * *